US006323347B2

(12) United States Patent
Chen et al.

(10) Patent No.: US 6,323,347 B2
(45) Date of Patent: Nov. 27, 2001

(54) CATALYST FOR PREPARING LACTONE AND A METHOD FOR PREPARING LACTONE

(75) Inventors: Shien-Chang Chen, Taipei; Fu-Shen Lin, Kaohsiung; Liang-An Hsu, Kaohsiung; Cheng-Lin Tsai, Kaohsiung, all of (TW)

(73) Assignee: Dairen Chemical Corporation, Taipei (TW)

( * ) Notice: Subject to any disclaimer, the term of this patent is extended or adjusted under 35 U.S.C. 154(b) by 0 days.

(21) Appl. No.: 09/737,894

(22) Filed: Dec. 15, 2000

(30) Foreign Application Priority Data

Jan. 14, 2000 (TW) ................................................ 89100512

(51) Int. Cl.[7] ...................... C07D 307/32; C07D 313/04; C07D 305/12; B01J 37/00
(52) U.S. Cl. .......................... 549/295; 549/266; 549/263; 549/328; 502/104; 502/106
(58) Field of Search ................................... 549/295, 263, 549/266, 328; 502/104, 106

(56) References Cited

U.S. PATENT DOCUMENTS 5,110,954   5/1992   Bellis .

FOREIGN PATENT DOCUMENTS

| 58-13575 | 1/1983 | (JP) . |
| 61-246173 | 11/1986 | (JP) . |
| 2-255668 | 10/1990 | (JP) . |
| 3-232874 | 10/1991 | (JP) . |

*Primary Examiner*—Charanjit S. Aulakh
(74) *Attorney, Agent, or Firm*—Michael Best & Friedrich LLP

(57) ABSTRACT

The present invention relates to a catalyst for preparing a lactone, which is prepared by supporting a cupric compound, a zinc compound and at least one alkaline earth metal compound on the supporter. The present invention also relates to a method for preparing a lactone, which comprises a dehydrocyclization reaction of a diol under a gas phase in the presence of the aforementioned catalyst after activating said catalyst. The catalyst for preparing lactone of the present invention is quite economic because of its high activity, long lifetime and high selectivity of products.

18 Claims, No Drawings

CATALYST FOR PREPARING LACTONE AND A METHOD FOR PREPARING LACTONE

FIELD OF THE INVENTION

The present invention relates to a catalyst for preparing a lactone, which is prepared by supporting a cupric compound, a zinc compound and at least one alkaline earth metal compound on the supporter. The present invention also relates to a method for preparing a lactone, which comprises a dehydrocyclization reaction of a diol under a gas phase in the presence of the aforementioned catalyst after activating said catalyst.

BACKGROUND OF THE INVENTION

Lactone, such as γ-butyrolactone, may be used as a herbicide, used in the pharmaceutical composition, or used for preparing an intermediate; this intermediate is used to prepare pyrrolidone (such as N-methylpyrrolidone, 2-pyrrolidone and N-vinylpyrrolidone), piperidine, phenyl-butyric acid and thiobutyric acid. Thus, developing an economic method for preparing γ-butyrolactone is a common industrial requirement.

Previously, γ-butyrolactone was commonly produced by a hydrogenation reaction with maleic anhydride or maleic acid ester under liquid phase or gas phase. However, this is an undesirable industrial process because the process needs a lot of hydrogen gas and its catalyst has a short lifetime.

Recently, γ-butyrolactone was produced by a dehydrocyclization reaction with 1,4-butanediol, where a hydrogen by-product was generated as a raw material and as fuel. This method for preparing γ-butyrolactone through the dehydrocyclization reaction of 1,4-butanediol is disclosed in Japanese Patent Unexamined Publication No. Sho-58-13575, wherein the dehydrocyclization reaction is carried out under liquid phase using a platinum/lead catalyst; however, the activity of said catalyst is low and the selectivity of γ-butyrolactone is also low. The method disclosed in Japanese Patent Unexamined Publication No. Sho-61-246173 describes that γ-butyrolactone is obtained by passing 1,4-butanediol vapor through a copper/chromium/zinc catalyst; however, this method may generate many tetrahydrofuran and butanol by-products, and the selectivity and yield of γ-butyrolactone is usually low. The method disclosed in Japanese Patent Unexamined Publication No. Hei-3-232874 describes that γ-butyrolactone is produced by passing 1,4-butanediol vapor through a copper/chromium/manganese or barium catalyst; the method disclosed in U.S. Pat. No. 5,110,954 describes that γ-butyrolactone is obtained by adding 1,4-butanediol into the solution of copper/chromium catalyst; and the method disclosed in Japanese Patent Unexamined Publication No. Hei-2-255668 describes that γ-butyrolactone is produced by passing 1,4-butanediol vapor through a copper/zinc/alkali metal catalyst. However, the activity of these catalysts may decay quickly, and the conversion of 1,4-butylene glycol may become lower after reacting over a long period. Therefore, it is undesirable as an industrial process.

The present inventors have deeply studied the above defects of the traditional technique and found more effective catalyst for preparing a lactone in the catalyst supporting a cupric compound, a zinc compound and at least one alkaline earth metal compound. The process for preparing lactone through the dehydrocyclization reaction of diol using the above catalyst under gas phase may increase the activity and lifetime of catalyst, while the selectivity may be up to 99 mol % or more; therefore the beneficial economic effect of industrial processes may be substantially increased. We have hereby accomplished the present invention.

SUMMARY OF THE INVENTION

The present invention relates to a catalyst for preparing a lactone, which is prepared by supporting a cupric compound, a zinc compound and at least one alkaline earth metal compound on the supporter. The present invention also relates to a method for preparing a lactone, which comprises a dehydrocyclization reaction of a diol under a gas phase in the presence of the aforementioned catalyst after activating said catalyst. The catalyst for preparing lactone of the present invention is quite economic because of its high activity, long lifetime and high selectivity of products.

DETAILED DESCRIPTION OF THE INVENTION

The catalyst of the present invention used for preparing a lactone is prepared by supporting a cupric compound, a zinc compound and at least one alkaline earth metal compound on the supporter. The suitable materials for the supporter used in the catalyst of the present invention are silica, alumina, or their mixture, more preferably the mixture of silica and alumina.

In the catalyst of the present invention used for preparing lactone, the cupric compound may be various cupric salts, of which the examples are copper (II) nitrate ($Cu(NO_3)_2 \cdot 3H_2O$), copper (II) carbonate ($Cu_2(OH)_2CO_3$), copper (II) acetate ($Cu(CH_3COO)_2$), copper (II) chloride ($CuCl_2 \cdot 2H_2O$), copper (II) hydroxide ($Cu(OH)_2$), copper (II) phosphate ($Cu_3(PO_4)_2 \cdot 3H_2O$), copper (II) sulfate ($CuSO_4 \cdot 5H_2O$), etc. The zinc compound used in the catalyst of the present invention may be various zinc salts, of which the example are zinc nitrate ($Zn(NO_3)_2 \cdot 6H_2O$), zinc carbonate ($ZnCO_3$), zinc acetate ($Zn(CH_3COO)_2 \cdot 2H_2O$), zinc chloride ($ZnCl_2$), zinc hydroxide ($Zn(OH)_2$), zinc sulfate ($ZnSO_4 \cdot 7H_2O$), etc. The alkaline earth metal compound used in the catalyst of the present invention is at least one selected from a metal compound consisting of beryllium, magnesium, calcium, strontium and barium, and more preferably at least one selected from a metal compound consisting of magnesium, calcium and barium, which comprises their carbonate, hydroxide, silicate, phosphate, etc.

The catalyst of the present invention used for preparing a lactone is prepared according to the following method. The supporter is immersed in the above aqueous cupric salt and zinc salt solutions, and the value of pH is adjusted between 8 and 11 using ammonia water, while the hydroxides of copper and zinc are precipitated on the supporter. The precipitate is washed with water and dried. The precipitate is immersed in the above aqueous salts solution selected from one or two alkaline earth metal compound(s) consisting of magnesium, calcium and barium, and then calcined for 3 to 5 hours at 400 to 500° C. If it is necessary, a mold-aid agent such as graphite may be added, and a predeterminate shape is molded by a molding machine. In such resultant catalyst, each metal component exists in the form of oxide. Therefore, before the dehydrogenation reaction of diol, the catalyst must be reduced and be activated at a temperature ranging from 180 to 250° C. for 6 to 20 hours with hydrogen gas wherein the ratio of hydrogen gas to nitrogen gas starts between 1:20 and 1:10 by volume, then gradually adjusts to all hydrogen gas.

In the catalyst of the present invention used for preparing lactone, the ratio of copper (II) oxide to zinc oxide is usually 6:1 to 1:2 by weight, preferably 5:1 to 1:1. When any one of the alkaline earth metal compounds selected from a group consisting of magnesium, calcium and barium is used, its amount is preferably 0.01 to 10 wt %, more preferably 0.05 to 5 wt %, based on the total weight of copper (II) oxide and zinc oxide in terms of oxides. When any two of the alkaline earth metal compounds selected from a group consisting of magnesium, calcium and barium is used, their amounts are preferably 0.5 to 20 wt %, more preferably 1 to 10 wt %, based on the total weight of copper (II) oxide and zinc oxide in terms of oxides. The amount of support is preferably 0.5 to 20 wt %, more preferably 1 to 10 wt %, based on the total weight of copper (II) oxide and zinc oxide in terms of silica.

The present invention also relates to a method for preparing a lactone, which comprises a dehydrocyclization reaction of a diol under a gas phase in the presence of the aforementioned catalyst after activating said catalyst.

The example of the lactone used in the method for preparing lactone of the present invention includes, for instance, β-propiolactone, β-butyrolactone, γ-butyrolactone, γ-valerolactone, δ-butyrolactone, γ-caprolactone, ε-caprolactone, δ-hydroxyoctylic acid lactone, δ-hydroxynonylic acid lactone, γ-hydroxydecylic acid lactone, δ-hydroxydecylic acid lactone, etc.

The example of the diol used in the method for preparing lactone of the present invention includes, for instance, 1,3-propylene glycol, 2-methyl-1,3-propylene glycol, 1,3-butylene glycol, 1,4-butylene glycol, 1,5-pentanediol, 1,4-petanediol, 1,5-hexanediol, 1,6-hexanediol, 1,7-heptanediol, 1,8-octanediol, 1,9-nonanediol, 1,10-decanediol, etc.

In the dehydrocyclization reaction of the method for preparing lactone such as γ-butyrolactone used in the present invention, the reaction temperature usually ranges from 160 to 280° C., preferably 180 to 250° C. If the reaction temperature is too low, the conversion of 1,4-butylene glycol may be decreased. Although the higher temperature may increase the conversion of 1,4-butylene glycol, the selectivity of γ-butyrolactone may be substantially decreased.

In the dehydrocyclization reaction of the method for preparing lactone such as γ-butyrolactone used in the present invention, the reaction pressure usually ranges from 0 to 10 atm., preferably from 1 to 5 atm. However, ahe higher reaction pressure may easily carry out an undesired reaction, decreasing the yield.

In the dehydrocyclization reaction of the method for preparing lactone such as γ-butyrolactone used in the present invention, the hydrogen gas is needed as a carrier gas. If the hydrogen gas do not exist in the reaction system, the lifetime of catalyst may be shortened. The amount of hydrogen gas must at least maintain the reaction system in gas phase. In generally, the molar ratio of hydrogen gas to 1,4-butylene glycol used in the present invention ranges from (12 to 1):1, preferably from (8 to 1.5):1.

In the dehydrocyclization reaction of the method for preparing lactone such as γ-butyrolactone used in the present invention, if the gas hourly space velocity of 1,4-butylene glycol is too low, the retention time of gas in the catalyst bed is also too long so that the product may be decomposed, resulting in the decreasing selectivity of γ-butyrolactone. If the gas hourly space velocity of 1,4-butylene glycol is too high, the retention time of gas in the catalyst bed is also too short so that the conversion of 1,4-butylene glycol decreases. In general, the gas hourly space velocity of 1,4-butylene glycol ranges from 10 to 20,000 hr$^{-1}$, preferably 30 to 9,000 hr$^{-1}$.

In the dehydrocyclization reaction of the method for preparing lactone such as γ-butyrolactone used in the present invention, the catalyst bed may be a fixed bed or a fluid bed.

The present invention will be further described in the following Examples and Comparative Examples. However, the scope of the present invention is not restricted by such Examples.

EXAMPLE

In a given time after the dehydrocyclization reaction, the product was collected by condensation. The component of the efflux from the outlet was analyzed by HP-6890 gas chromatograph. The conversion of diol and the selectivity of lactone were calculated according to the following equation (1) and (2), and the yield of lactone is also obtained:

$$\text{The Conversion of Diol (\%)} = \frac{\text{The Mole of Feed-in Diol} - \text{The Mole of Feed-out Diol}}{\text{The Mole of Feed-in Diol}} \times 100\% \quad (1)$$

$$\text{The Selectivity of Lactone (\%)} = \frac{\text{The Mole of Lactone Product}}{\text{The Mole of Feed-in Diol} - \text{The Mole of Feed-out Diol}} \times 100\% \quad (2)$$

Reference Example 1

A commercially available copper-chromium catalyst (30 ml) (wherein copper oxide was 42 wt %, chromium oxide was 28 wt %, and a diameter was 5 mm) was packed in the stainless steel reactor having an inside diameter of 23.5 mm. After the temperature was elevated to 150° C. with nitrogen gas, the mixed gas of 10 vol % hydrogen gas was passed into the reactor, then the catalytic reduction reaction was initiated. The temperature and the concentration of hydrogen gas were gradually elevated until the reduction temperature of catalyst was 200° C. and the concentration of hydrogen gas was 100 vol %. When the temperature of catalyst bed was confirmed to be the same as that of th heating equipment, the reduction reaction was terminated.

Subsequently, the temperature of the reactor was elevated to 210° C. 1,4-butylene glycol was pumped into the reactor using a quantitative pump, and the gas hourly space velocity of 1,4-butylene glycol was maintained at 4500 hr$^{-1}$. After the dehydrogenation reaction was carried out at a hydrogen gas/1,4-butylene glycol ratio of 5 mole:1 mole, the product was collected and analyzed. The results are shown in Table 1.

Reference Example 2

The same steps as in Reference Example 1 were repeated, but a commercially available copper-zinc catalyst (G-66) was used, wherein the component was 60 wt % of copper oxide and 30 wt % of zinc oxide. The results are shown in Table 1.

Reference Example 3

The same steps as in Reference Example 1 were repeated, but a copper/chromium/zinc catalyst which was prepared by the method of Japanese Patent Unexamined Publication No. Hei-61-246173 was used, wherein the component was 35 wt % of copper oxide, 4.5 wt % of zinc oxide and 60 wt % of chromium oxide. The results are shown in Table 1.

Reference Example 4

The same steps as in Reference Example 1 were repeated, but a commercially available copper-zinc catalyst (G-66) which was immersed in 0.5 wt % of aqueous sodium hydroxide solution and then dried was used, wherein the component was 60 wt % of copper oxide, 30 wt % of zinc oxide and 0.12 wt % of sodium hydroxide. The results are shown in Table 1.

TABLE 1

| Reference Example | 1 | 2 | 3 | 4 |
|---|---|---|---|---|
| Reaction Temperature (° C.) | 210 | 210 | 210 | 210 |
| Reaction Pressure (atm) | 1 | 1 | 1 | 1 |

TABLE 1-continued

| Reference Example | 1 | 2 | 3 | 4 |
|---|---|---|---|---|
| Gas Hourly Space Velocity of 1,4-Butylene Glycol (hr$^{-1}$) | 4500 | 4500 | 4500 | 4500 |
| Molar Ratio of Hydrogen Gas to 1,4-Butylene Glycol | 5/1 | 5/1 | 5/1 | 5/1 |
| Conversion of 1,4-Butylene Glycol (mol %) | 72.50 | 91.50 | 81.30 | 97.20 |
| Selectivity of γ-Butyrolactone (mol %) | 88.30 | 92.50 | 90.50 | 95.30 |
| Yield of γ-Butyrolactone (mol %) | 64.02 | 84.64 | 73.82 | 92.63 |

Example 1

60 wt % of aqueous copper nitrate solution (350 g) was slowly poured into 40 wt % of aqueous zinc nitrate solution (220 g) and the powder of silica (10 g) wherein the BET surface area was 185 m$^2$/g (said surface area was measured according to the Brunner-Emmett-Teller Method), and the mixture was stirred vigorously. Subsequently, 25 wt % of ammonia water was added to maintain the pH value of the mixed aqueous solution at 10 while the mixture was still stirred. The precipitate was filtered and separated, washed with water, and placed into a oven to dry at 100° C. for 12 hours, after which time a catalyst precursor was obtained. This catalyst precursor was moved to a tubular high-temperature furnace, heated to 450° C., and calcined for 4 hours. The component of this catalyst was at a copper oxide/zinc oxide ratio of 3:1.

1.0 wt % of graphite was added to the above catalyst, then that catalyst was extruded to a roundly granular catalyst having a diameter of 5 mm. The same steps as in Reference Example 1 were repeated with this catalyst (30 ml). The results are shown in Table 2.

Example 2 to 7

The same steps as in Example 1 were repeated, but the ratio by weight of copper oxide to zinc oxide, the temperature of dehydrogenation, and the molar ratio of hydrogen gas to 1,4-butylene glycol are all shown in Table 2. The results of Table 2 are as follows.

TABLE 2

| Example | 1 | 2 | 3 | 4 | 5 | 6 | 7 |
|---|---|---|---|---|---|---|---|
| Ratio by Weight of Cupric Oxide to Zinc Oxide | 3/1 | 5/1 | 1/2 | 5/1 | 3/1 | 5/1 | 3/1 |
| Reaction Temperature (° C.) | 210 | 210 | 210 | 210 | 210 | 230 | 230 |
| Reaction Pressure (atm) | 1 | 1 | 1 | 1 | 1 | 1 | 1 |
| Gas Hourly Space Velocity of BOD (hr$^{-1}$) | 4500 | 4500 | 4500 | 4500 | 4500 | 4500 | 4500 |
| Molar Ratio of Hydrogen Gas to BOD | 5/1 | 5/1 | 5/1 | 2/1 | 2/1 | 5/1 | 5/1 |
| Conversion of BOD (mol %) | 97.30 | 98.50 | 92.10 | 95.30 | 93.50 | 98.10 | 97.20 |
| Selectivity of γ-Butyrolactone (mol %) | 96.10 | 97.40 | 90.50 | 97.10 | 96.50 | 91.50 | 90.30 |
| Yield of γ-Butyrolactone (mol %) | 93.50 | 95.94 | 83.35 | 92.53 | 90.22 | 89.76 | 87.77 |

Example 8

The catalyst precursor prepared by Example 1 was immersed in 1.5 wt % of aqueous barium hydroxide solution. Then, this catalyst was moved to a tubular high-temperature furnace, heated to 450° C., and calcined for 4 hours. The component of this catalyst was 55 wt % of copper oxide, 22 wt % of zinc oxide and 1.2 wt % of barium oxide.

The same steps as in Reference Example 1 were carried out with this catalyst. The results are shown in Table 3.

Example 9

The catalyst precursor prepared by Example 1 was immersed in 1.0 wt % of aqueous calcium hydroxide solution. Then, this catalyst was moved to a tubular high-temperature furnace, heated to 450° C., and calcined for 4 hours. The component of this catalyst was 53 wt % of copper oxide, 24 wt % of zinc oxide and 0.81 wt % of calcium oxide.

The same steps as in Reference Example 1 were carried out with this catalyst. The results are shown in Table 3.

Example 10

The catalyst precursor prepared by Example 1 was immersed in 1.0 wt % of aqueous magnesium hydroxide solution. Then, this catalyst was moved to a tubular high-temperature furnace, heated to 450° C., and calcined for 4 hours. The component of this catalyst was 49 wt % of copper oxide, 26 wt % of zinc oxide and 0.52 wt % of magnesium oxide.

The same steps as in Reference Example 1 were carried out with this catalyst. The results are shown in Table 3.

Example 11

The catalyst precursor prepared by Example 1 was immersed in 1.5 wt % of aqueous barium hydroxide solution and 0.3 wt % of aqueous calcium hydroxide solution. Then, this catalyst was moved to a tubular high-temperature furnace, heated to 450° C., and calcined for 4 hours. The component of this catalyst was 55 wt % of copper oxide, 22 wt % of zinc oxide, 1.2 wt % of barium oxide and 0.14 wt % of calcium oxide.

The same steps as in Reference Example 1 were carried out with this catalyst. The results are shown in Table 3.

Example 12

The catalyst precursor prepared by Example 1 was immersed in 1.0 wt % of aqueous calcium hydroxide solution and 0.4 wt % of aqueous magnesium hydroxide solution. Then, this catalyst was moved to a tubular high-temperature furnace, heated to 450° C., and calcined for 4 hours. The component of this catalyst was 53 wt % of copper oxide, 24 wt % of zinc oxide, 0.81 wt % of calcium oxide and 0.16 wt % of magnesium oxide.

The same steps as in Reference Example 1 were carried out with this catalyst. The results are shown in Table 3.

Example 13

The catalyst precursor prepared by Example 1 was immersed in 1.0 wt % of aqueous magnesium hydroxide solution and 0.2 wt % of aqueous barium hydroxide solution. Then, this catalyst was moved to a tubular high-temperature furnace, heated to 450° C., and calcined for 4 hours. The component of this catalyst was 49 wt % of copper oxide, 26 wt % of zinc oxide, 0.52 wt % of magnesium oxide and 0.11 wt % of barium oxide.

The same steps as in Reference Example 1 were carried out with this catalyst. The results are shown in Table 3.

TABLE 3

| Example | 8 | 9 | 10 | 11 | 12 | 13 |
|---|---|---|---|---|---|---|
| Reaction Temperature (° C.) | 210 | 210 | 210 | 210 | 210 | 210 |
| Reaction Pressure (atm) | 1 | 1 | 1 | 1 | 1 | 1 |
| Gas Hourly Space Velocity of BOD (hr$^{-1}$) | 4500 | 4500 | 4500 | 4500 | 4500 | 4500 |
| Molar Ratio of Hydrogen Gas to BOD | 5/1 | 5/1 | 5/1 | 5/1 | 5/1 | 5/1 |
| Conversion of BOD (mol %) | 99.50 | 99.20 | 99.60 | 99.90 | 99.50 | 99.80 |
| Selectivity of γ-Butyrolactone (mol %) | 99.10 | 98.60 | 98.10 | 99.80 | 99.10 | 99.30 |
| Yield of γ-Butyrolactone (mol %) | 98.60 | 97.81 | 97.70 | 99.70 | 98.60 | 99.10 |

What is claimed is:

1. A catalyst for preparing a lactone, which is prepared by supporting a cupric compound, a zinc compound and at least one alkaline earth metal compound on the supporter.

2. A catalyst according to claim 1, wherein the material of said supporter is selected from a group consisting of silica, alumina, and their mixture.

3. A catalyst according to claim 1, wherein said cupric compound is selected from a group consisting of copper (II) nitrate, copper (II) carbonate, copper (II) acetate, copper (II) chloride, copper (II) hydroxide, copper (II) phosphate and copper (II) sulfate.

4. A catalyst according to claim 1, wherein said zinc compound is selected from a group consisting of zinc nitrate, zinc carbonate, zinc acetate, zinc chloride, zinc hydroxide and zinc sulfate.

5. A catalyst according to claim 1, wherein said alkaline earth metal compound is selected from a group consisting of carbonate, hydroxide, silicate and phosphate of beryllium, magnesium, calcium, strontium or barium.

6. A catalyst according to claim 1, wherein the ratio of cupric compound to zinc compound is 6:1 to 1:2 by weight in terms of copper (II) oxide and zinc oxide.

7. A catalyst according to claim 1, wherein the amount of alkaline earth metal compound is 0.01 to 10 wt % based on the total weight of copper (II) oxide and zinc oxide in terms of oxides, when one of the alkaline earth metal compounds selected from a group consisting of magnesium, calcium and barium is used.

8. A catalyst according to claim 1, wherein the amount of alkaline earth metal compound is 0.5 to 20 wt % based on the total weight of copper (II) oxide and zinc oxide in terms of oxides, when two of the alkaline earth metal compounds selected from a group consisting of magnesium, calcium and barium are used.

9. A method for preparing a lactone, which comprises a dehydrocyclization reaction of a diol under a gas phase in the presence of a catalyst according to any one of claim 1 to claim 8 after activating said catalyst.

10. A method according to claim 9, wherein said lactone is selected from a group consisting of β-propiolactone, β-butyrolactone, γ-butyrolactone, γ-valerolactone, δ-butyrolactone, γ-caprolactone, ε-caprolactone, δ-hydroxyoctylic acid lactone, δ-hydroxynonylic acid lactone, γ-hydroxydecylic acid lactone and δ-hydroxydecylic acid lactone.

11. A method according to claim 9, wherein said diol is selected from a group consisting of 1,3-propylene glycol, 2-methyl-1,3-propylene glycol, 1,3-butylene glycol, 1,4-butylene glycol, 1,5-pentanediol, 1,4-petanediol, 1,5-hexanediol, 1,6-hexanediol, 1,7-heptanediol, 1,8-octanediol, 1,9-nonanediol and 1,10-decanediol.

12. A method according to claim 9, wherein said lactone is γ-butyrolactone and said diol is 1,4-butylene glycol.

13. A method according to claim 9, wherein said catalyst is reduced to activate at a temperature ranging from 180 to 250° C. for 6 to 20 hours with hydrogen gas.

14. A method according to claim 9, wherein said dehydrocyclization reaction is carried out at a temperature ranging from 160 to 280° C.

15. A method according to claim 12, wherein said dehydrocyclization reaction is carried out in a molar ratio of hydrogen gas to 1,4-butylene glycol ranging from (12 to 1):1.

16. A method according to claim 12, wherein said dehydrocyclization reaction is carried out with the gas hourly space velocity of 1,4-butylene glycol ranging from 10 to 20,000 hr$^{-1}$.

17. A method according to claim 9, wherein the catalyst bed used for said dehydrocyclization reaction is a fixed bed.

18. A method according to claim 9, wherein the catalyst bed used for said dehydrocyclization reaction is a fluid bed.

* * * * *